(12) United States Patent
Latham

(10) Patent No.: US 8,192,601 B2
(45) Date of Patent: Jun. 5, 2012

(54) ELECTROBLOTTING CASSETTE WITH MANUALLY RELEASABLE ELECTRODES OF ADJUSTABLE SPACING

(75) Inventor: Matthew Latham, Dixon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 318 days.

(21) Appl. No.: 12/708,672

(22) Filed: Feb. 19, 2010

(65) Prior Publication Data

US 2010/0213064 A1 Aug. 26, 2010

Related U.S. Application Data

(60) Provisional application No. 61/154,536, filed on Feb. 23, 2009.

(51) Int. Cl.
*B01D 57/02* (2006.01)
*G01N 33/559* (2006.01)

(52) U.S. Cl. ............ 204/456; 204/464; 204/462

(58) Field of Classification Search ............ 204/614, 204/450–470, 547, 606; 220/324, 315, 284, 220/326, 4.07, 4.26, 4.34; 206/506, 507, 206/511, 708, 722, 723, 487, 488, 489
See application file for complete search history.

(56) References Cited

U.S. PATENT DOCUMENTS

| 6,296,752 | B1 | 10/2001 | McBride et al. |
| 2002/0157953 | A1* | 10/2002 | Chen ............... 204/614 |
| 2004/0195103 | A1 | 10/2004 | Zhou |
| 2007/0284250 | A1 | 12/2007 | Magnant et al. |

* cited by examiner

*Primary Examiner* — Jeffrey T Barton
*Assistant Examiner* — Steven Rosenwald
(74) *Attorney, Agent, or Firm* — Kilpatrick Townsend & Stockton LLP.; M. Henry Heines

(57) ABSTRACT

An electroblotting cassette is formed in three separable parts—an upper plate, a lower plate, and a base that receives both plates, with electrodes mounted on both the upper and lower plates. The cassette accommodates transfer stacks of different thicknesses by its inclusion of a set of raised areas, known as "lands," on the floor of the base and a set of inverse lands on the underside of the lower electrode plate, the two sets being spatially arranged to either abut each other or be offset from each other, depending on the orientation of the lower plate, thereby allowing the user a choice between two heights of the lower plate within the base and hence two thicknesses of transfer stacks. Other arrangements include those with more than one set of lands on one or both parts to allow for three or more thickness selections, or depressions in place of lands. Finger-operated latches secure the upper plate to the base.

12 Claims, 7 Drawing Sheets

US 8,192,601 B2

ELECTROBLOTTING CASSETTE WITH MANUALLY RELEASABLE ELECTRODES OF ADJUSTABLE SPACING

CROSS-REFERENCE TO RELATED APPLICATION

This application claims the benefit of U.S. Provisional Patent Application No. 61/154,536, filed Feb. 23, 2009, the contents of which are incorporated herein by reference.

FIELD OF THE INVENTION

This invention resides in the field of gel electrophoresis, and relates in particular to the transfer of electrophoretically separated species from a slab gel in which the species are separated to a sheet-form support matrix in which the species can be detected, identified, and quantified.

DESCRIPTION OF THE PRIOR ART

Proteins, nucleic acids, or other biological species that have been electrophoretically separated in an slab gel are often transferred to a membrane of nitrocellulose, nylon, polyvinyl difluoride, or similar materials for identification and quantification, since such analyses are more easily performed on the membrane than in the gel. One widely used transfer technique is electroblotting, in which the flat surfaces of the gel and membrane are placed in full direct contact and an electric current is passed through them in a direction transverse to the gel and membrane, thereby effecting transfer in a manner similar to that by which the species were mobilized within the gel. When the species are DNA fragments, the transfer is termed a Southern blot after its originator, the British biologist Edwin M. Southern. By analogy, the transfer of RNA fragments is termed Northern blotting, and the transfer of proteins or polypeptides is termed Western blotting. Once transfer has occurred, the species on the membrane are analyzed by methods appropriate to the species themselves. In Southern and membrane are analyzed by methods appropriate to the species themselves. In Southern and Northern blots, for example, the analysis involves treatment of the species on the membrane with a hybridization probe, followed by labeling the probe with a fluorescent or chromogenic dye. In Western blots, the analysis involves treatment of the species with antibodies, followed by the labeling of the antibodies with fluorescent or chromogenic dyes, enzymes, or other labeling techniques commonly used for detecting the antibodies.

Electroblotting of either the Southern, Northern, or Western type can be performed in either a wet, dry, or semi-dry format. In wet blotting, buffer solutions are placed between the electrode and the gel or membrane to provide the ions needed to transmit the electric current. In semi-dry blotting, the buffer solutions are replaced with filter papers wetted with the buffer solution, and the gel, membrane and filter papers are arranged in a transfer stack, also referred to as a "blotting sandwich," that consists of, in order, a first sheet of buffer-wetted filter paper, the blotting membrane, the gel, and a second sheet of buffer-wetted filter paper. Dry electroblotting uses no liquid buffers other than those residing in the gels. Descriptions of wet, dry, and semi-dry electroblotting and the associated materials and equipment are found in Margalit et al. (Invitrogen) United States Patent Application Publication No. US 2006/0278531 A1, published Dec. 14, 2006; Littlehales (American Bionetics) U.S. Pat. No. 4,840,714, issued Jun. 20, 1989; Dyson et al. (Amersham International) U.S. Pat. No. 4,889,606, issued Dec. 26, 1989; Schuette (Life Technologies, Inc.), U.S. Pat. No. 5,013,420, issued May 7, 1991; Chan et al. (Abbott Laboratories), U.S. Pat. No. 5,356,772, issued Oct. 18, 1994; Camacho (Hoefer Scientific Instruments), U.S. Pat. No. 5,445,723, issued Aug. 29, 2005; Boquet (Bertin & Cie), U.S. Pat. No. 5,482,613, issued Jan. 9, 1996; and Chen (Wealtec Enterprise Co., Ltd.) U.S. Pat. No. 6,592,734, issued Jul. 15, 2003.

SUMMARY OF THE INVENTION

The present invention resides in an electroblotting cassette, of particular value for use in semi-dry blotting, whose parts include a base, an upper plate, and a lower plate, with the two electrodes mounted on the upper and lower plates, respectively. The two plates are readily separable from the base and from each other, and can thus be individually cleaned or replaced without removing the electrodes from the plates. The plates are secured in the cassette by one or more manually releasable latches that secure the upper plate at a fixed height above the base. The cassette accommodates transfer stacks of different thicknesses however by features that allow the user to set the lower plate at any of various different heights above the base without changing the height of the upper plate above the base. A further feature of certain embodiments of the cassette of this invention is a construction that allows the cassette to be inserted into an electroblotting instrument that contains a power supply and electrical contacts to engage the electrodes in the cassette, and all other electrical components needed to perform the electroblotting. Still further features and embodiments will be apparent from the attached Figures and the description that follows.

DETAILED DESCRIPTION OF THE INVENTION AND PREFERRED EMBODIMENTS

Figure 1:
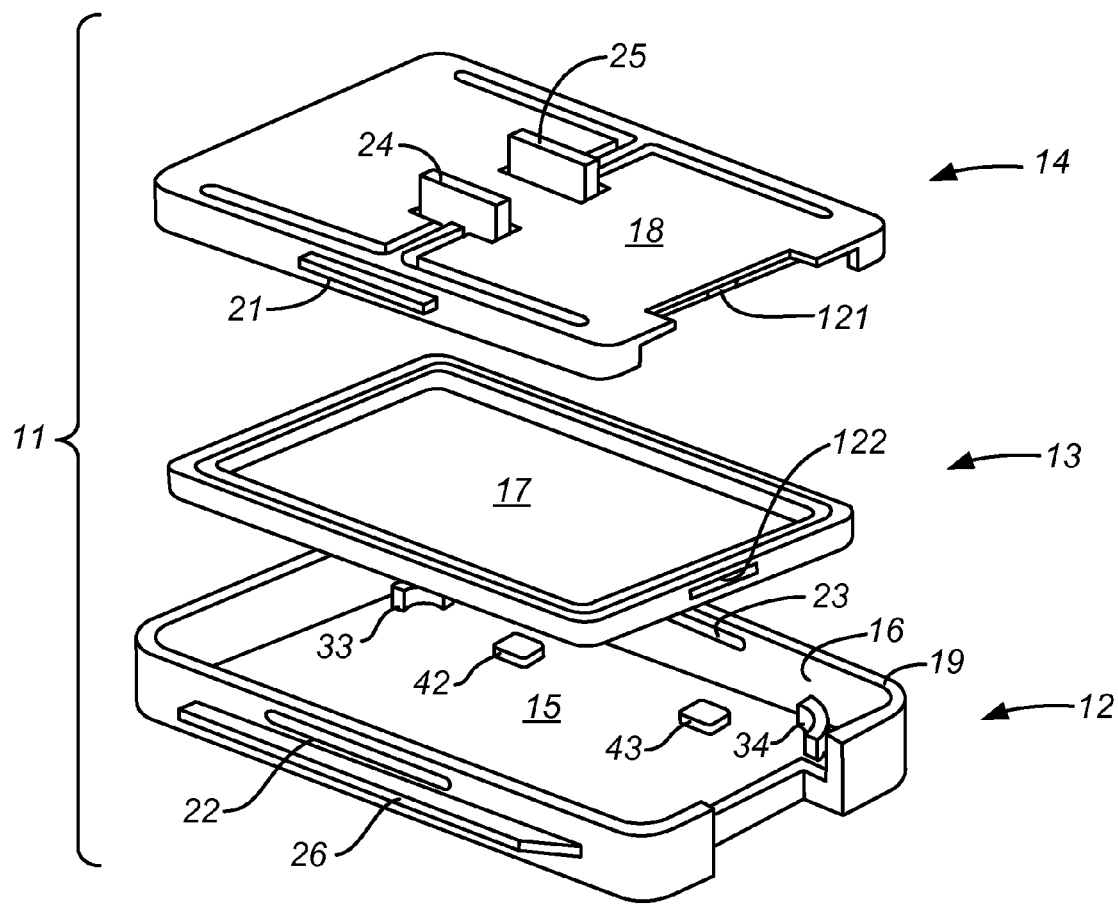
FIG. 1 is an exploded perspective view of an electroblotting cassette within the scope of the present invention.

The manually releasable latches of the present invention are features on one component of the apparatus that mate with, or generally engage, features on another component of the apparatus to join the two in such a manner that the position of one component with the respect to the other is substantially fixed and rigid while the features are so engaged, and are releasable from engagement by simple finger action or finger pressure of the user. The term "manually releasable" is used herein to denote that engagement and disengagement can be achieved without the use of tools, and preferably with a single action of the user's hand. Since the apparatus is designed to place the upper electrode at a distinct height above the base while allowing the lower electrode to reside at any of two or more different heights between the base and the upper electrode, the two components joined by the latches are preferably the upper plate and the base, with features on the upper plate mating with features on the base. The upper plate is preferably mounted to a support plate or frame of electrically non-conducting material, and the latch feature associated with the upper plate is thus preferably a feature of the support plate or frame. The latch features can be any conventional engaging features, such as a tab and slot combination, a hook and eye combination, a ledge and shelf combination, a ridge and groove combination, or a pin and aperture combination, and preferably any such combination that can be moved into and out of engagement by simple linear movement. A tab and slot combination is preferred. To stabilize the upper plate in a position parallel to the lower plate and the base, i.e., horizontal when in use, two or more latches are preferably distributed in a symmetrical arrangement on the cassette. In general, it will suffice to use two latches with one on each of two opposing sides of the cassette.

The terms "resilient" and "resiliently mounted" as used herein are intended to indicate that the structural aim or component on which the latch feature is mounted is generally stiff but bendable by application of an externally applied force, and once released from the force will return to its original shape and configuration. Thus, once a latch feature such as a tab, for example, is retracted by manual pressure and thus disengaged from its slot or other mating feature, the tab will return to its relaxed position when the pressure is released. When the upper plate is in position above the base with the lower plate between the two, the release of pressure on the latches will cause the latches to become engaged and the upper plate thus secured to the base. Finger action is preferably facilitated by the inclusion of lugs or knobs on the resilient members that can be grasped and manipulated to retract the latches.

The base is preferably constructed with raised side walls to contain the latch features at heights that will align the features with the corresponding features on the support or frame for the upper electrode plate. In preferred embodiments, the side walls encircle the entire base to contain both the lower and upper electrodes as well as any buffer solution that may flow from the gel or the membrane.

The cassette accommodates transfer stacks of different thicknesses by its inclusion of a set of raised areas, or flat-surfaced projections known in the art as "lands," on either the floor of the base, the undersurface of the lower electrode plate, or both, in conjunction with lands on, or indentations or depressions in, the opposing surface. Thus, when the lands are on the base floor, the opposing surface is the undersurface of the lower electrode plate, and when the lands are on the undersurface of the lower electrode plate, the opposing surface is the base floor. Different heights of the lower electrode plate above the base floor are achieved by different angular or rotational orientations of the lower electrode plate relative to the base, in conjunction with spatial arrangements and heights of the various lands, or depths of the various indentations or depressions. Changes in height are achieved by lands abutting opposing lands in one orientation vs. lands being offset from opposing lands in another orientation, or by lands abutting lands of a first height in one orientation and lands of a second (different) height in another orientation, or by lands abutting opposing lands or the floor in one orientation and lands falling in depressions in another orientation, or combinations of these changes. The changes can be illustrated by the simplest example of a set of lands on one surface and an opposing set on the other surface, the two sets being positioned asymmetrically about the axis of rotation (generally the center) of the upper plate. When the two sets of lands abut each other, distance of the lower electrode plate above the floor of the base is equal to the combined heights of the abutting lands, and when the two sets of lands are offset, i.e., the lands of one set clearing those of the other set, the lower electrode plate will sit lower in the cassette. Thus, by rotating the lower plate, the user can select between the different heights of the lower plate within the cassette while the height of the upper plate above the base remains the same.

In general, the lands, and depressions when present, are arranged on their respective surfaces in arrangements that are asymmetrical about the axis of rotation, and yet sufficient to define a plane in each orientation, such that rotation of the lower electrode plate (or its support) by a fractional rotation will result in a change in height. A fractional rotation of 180 degrees can thus provide a choice between two heights; a fractional rotation of 120 degrees can provide a choice among three heights; and as fractional rotation of 90 degrees can provide a choice among four heights. In preferred embodiments of the cassette, both the base and the upper and lower electrode plates are rectangular, which term is used herein to denote a parallelogram of which each corner is a right angle. The term "rectangular" thus includes a "square" (all sides of equal length) as well as an oblong rectangle, i.e., a rectangle whose length is greater than its width. Square shapes can be designed to provide fractional rotations of 90 degrees and thereby four angular positions, while oblong rectangles will provide only two angular positions separated by fractional rotations of 180 degrees. In all cases, stabilization in a plane can be achieved by as little as three contact points (lands or otherwise) distributed around the axis of rotation, such that for transfer stacks of all thicknesses, the cassette holds the electrodes parallel to each other.

Electroblotting cassettes in accordance with this invention preferably contain a feature that guides the insertion of the cassette into an instrument that contains the electrical connections for the blotting process. This guide feature can be a lateral shelf, ledge, shoulder, elongated tab, or series of tabs along the outer surface of each of two opposing sides of the cassette that will mate with a feature or features of complementary shape in the instrument interior. The instrument in which the cassette is placed can also contain two or more sets of such features to accommodate two or more cassettes in a stacking arrangement within the instrument, the stacked cassettes all powered by a common set of electrical components in the instrument.

While the novel features of the invention are capable of implementation in a variety of embodiments and designs, an understanding of the invention as a whole can be gained by a detailed study of specific examples. Such examples are shown in the Figures.

A single entire cassette 11 is shown in an exploded, perspective view in FIG. 1. The cassette 11 includes a base 12, a lower electrode plate 13, and an upper electrode plate 14. The base 12 has a floor 15 and a raised peripheral wall 16 to form a receptacle to receive both plates. The lower electrode 17 has an exposed, upward-facing surface, while the upper electrode has an exposed, downward-facing surface which is not visible in FIG. 1 since it is on the underside of the upper plate 14. When the cassette is fully assembled with a transfer stack (gel plus membrane) between the lower plate 13 and the upper plate 14 and the stack and both plates are positioned inside the base 12, the upper surface 18 of the upper plate 14 will be substantially co-planar with the upper rim 19 of the peripheral wall 16 of the base. This co-planarity is achieved by the construction and arrangement of the manually releasable latches, as described below.

One manually releasable latch is seen in full on the forward-facing longitudinal edge of the cassette. The components of this latch are a tab 21 protruding outwardly from the longitudinal edge of the upper plate 14 and a slot 22 in the corresponding location in the peripheral wall 16 of the base to receive the tab 21. A second tab (not visible) protrudes from the longitudinal edge of the upper plate on the opposite side, and a second slot 23 resides in a corresponding location in the peripheral wall 16 of the base. Both tabs when relaxed reside inside their respective slots, and retraction of the tabs from the slots is achieved by a pair of finger lugs 24, 25 protruding upward from the upper plate 14. Also visible in FIG. 1 is a laterally protruding elongated guide tab 26 that mates with a corresponding slot or ledge in the cavity of the instrument (not shown) in which the cassette is inserted for the power source and electrical components. The guide tab 26 extends from the outer surface of the longitudinal section of the peripheral side wall 16, and an identical but opposing guide tab (not visible) extends from the opposing longitudinal section, the two guide tabs being symmetrically arranged on the base.

Figure 2:
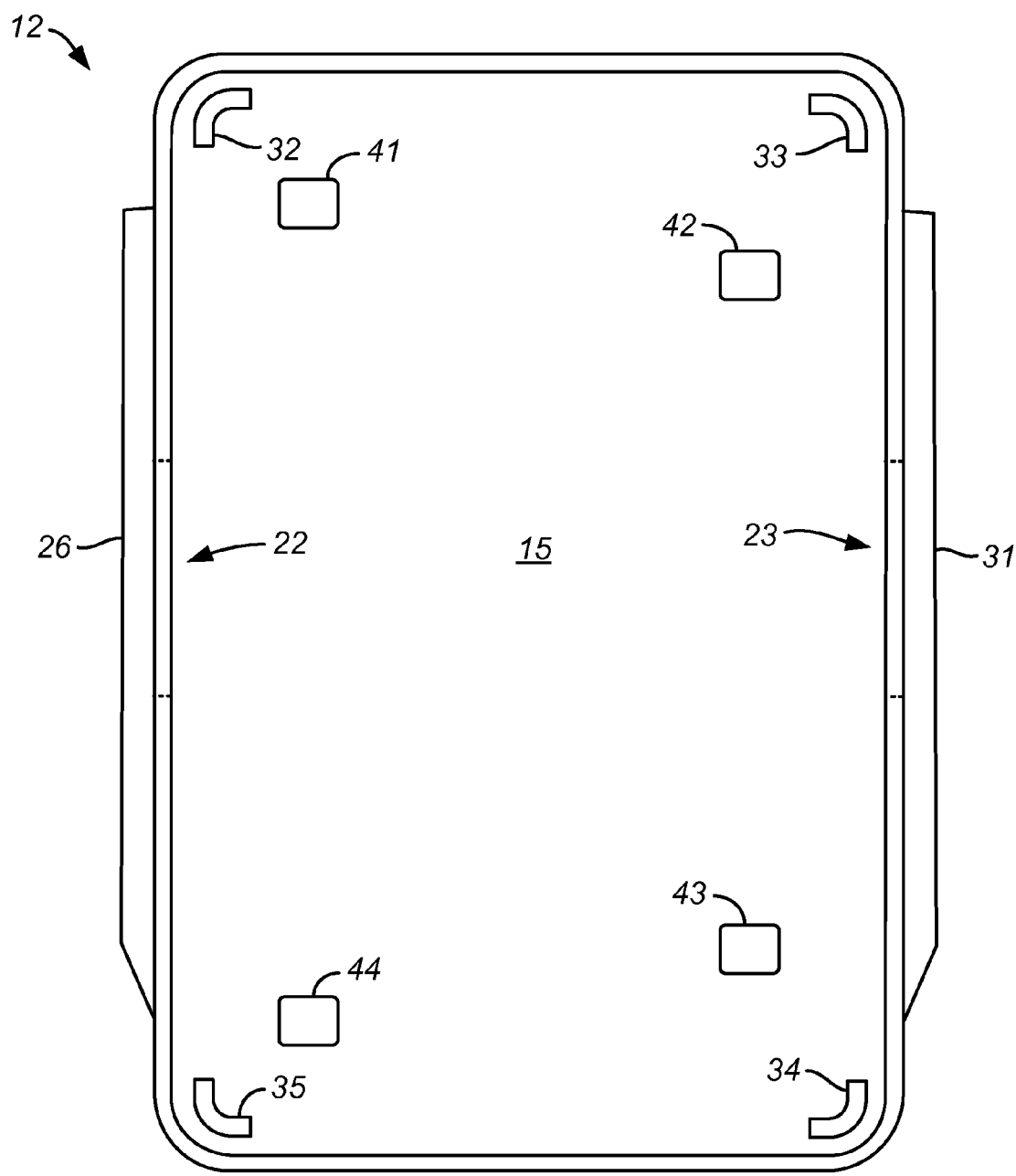
FIG. 2 is a plan view of the base of the cassette of FIG. 1.

FIG. 2 is a plan view of the base 12 showing features that are not visible in the perspective view of FIG. 1. Among these features is the second guide tab 31 which, together with the first guide tab 26, allows the user to slide the cassette into the instrument. The features also include a set of four corner guides 32, 33, 34, 35, each of which is a section of raised wall with a concave surface facing the center of the base. The spacing of the guides is selected to cause them to rest outside and receive the four corners of the lower electrode plate (not shown in this Figure), thereby centering the plate in the base. Two of the guides 33, 34 are also visible in FIG. 1. Still further features shown in FIG. 2 are a set of four "lands" (raised platforms) 41, 42, 43, 44 (two of which 42, 43 are also visible in FIG. 1). The four lands are not arranged at the corners of a rectangle but instead at the four corners of a trapezoid, so that corresponding inverse lands on the underside of the lower electrode plate will either reside directly above these lands or to the sides of (thereby clearing) these lands, depending on the orientation of the plate.

Figure 3:
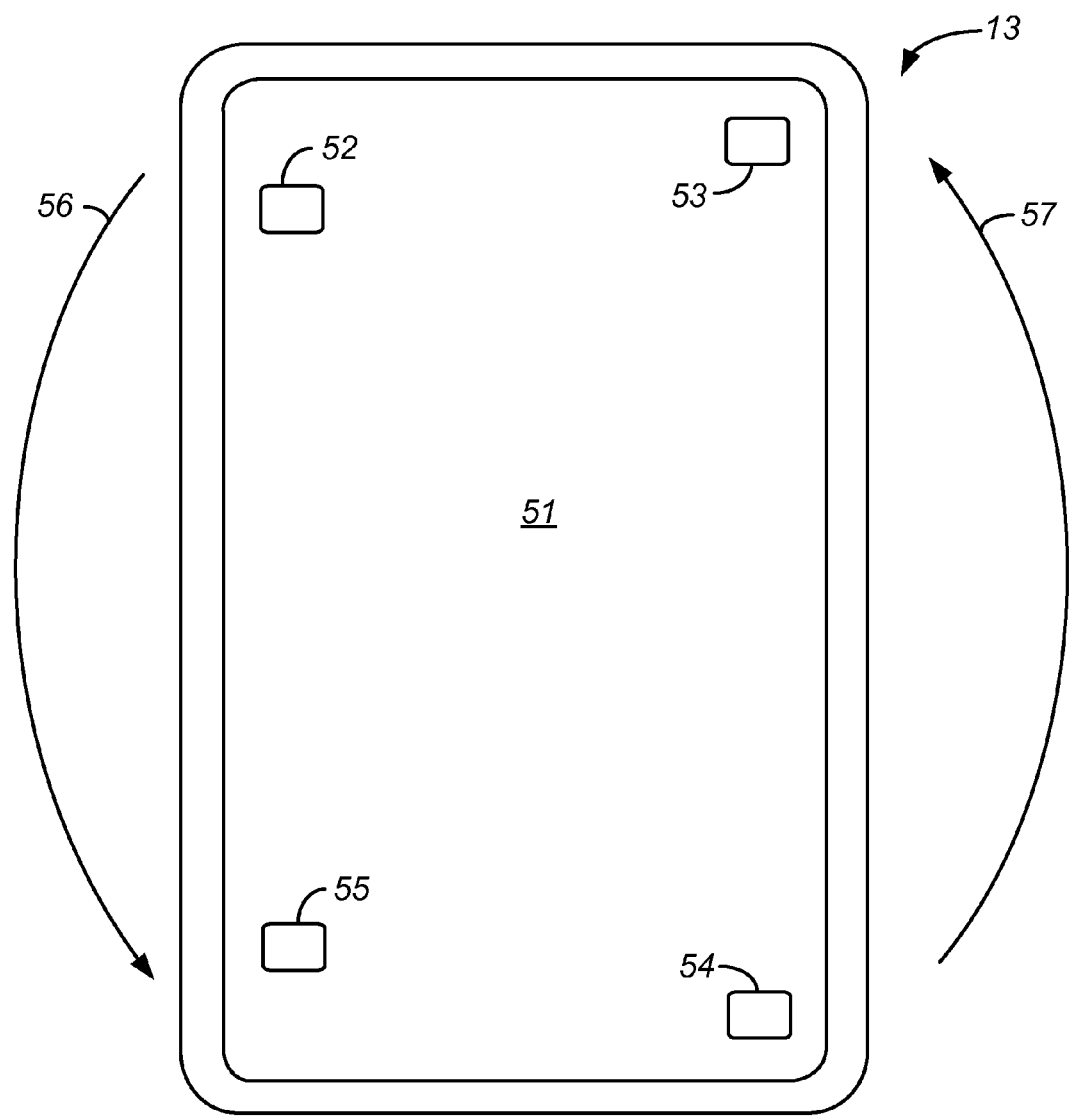
FIG. 3 is a plan view of the underside of the lower electrode plate of the cassette of FIG. 1.

FIG. 3 is a plan view of the underside of the lower electrode plate 13. The plate is a continuous rigid flat sheet 51 on whose upper surface the electrode (not visible in this view) resides. Inverse lands 52, 53, 54, 55 protrude downward from the bottom surface (i.e., the undersurface), and similarly to the lands 41, 42, 43, 44 of the base, these inverse lands are arranged at the corners of a trapezoid rather than a rectangle. The lands and the trapezoid are the same size as those of the base, and the lower plate can be set in the base in either of two orientations. In both orientations, the four corners of the lower plate will reside within the four corner guides 32, 33, 34, 35. In one orientation, the two sets of lands coincide, i.e., each inverse land in the set on the lower plate is directly opposite a corresponding land in the set on the base floor. In this orientation, the lower plate 13 will be at its maximum height in the base. If the user rotates the lower plate 180 degrees in the direction of the arrows 56, 57 in FIG. 3 before setting the lower plate inside the base, the second orientation is achieved. In this second orientation, the two sets of lands do not coincide but will instead clear each other, causing the lower plate 13 to sit lower in the base. Land arrangements other than trapezoids but with the same effect can be substituted, and the number of lands can be less or greater than four, as will be readily apparent to one skilled in the art and illustrated below.

Figure 4A:
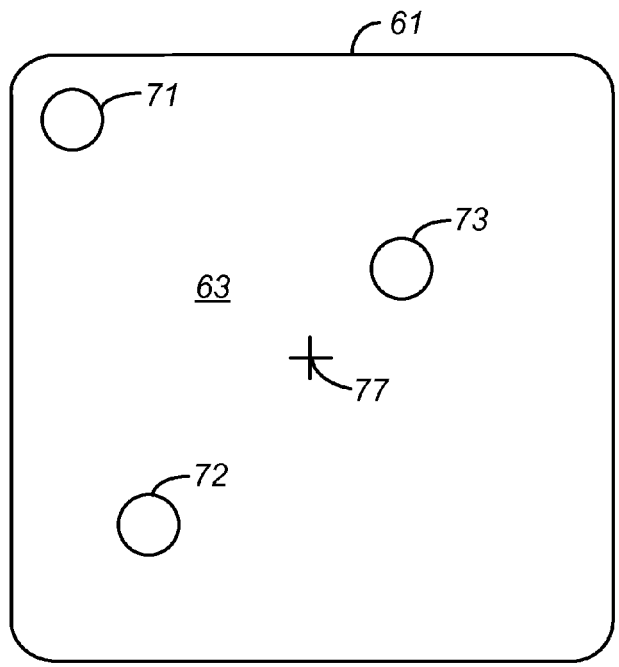
FIGS. 4A and 4B are plan views of the underside of the lower electrode plate and the floor of the base, respectively, of alternative designs to those of FIGS. 2 and 3.
Figure 4B:
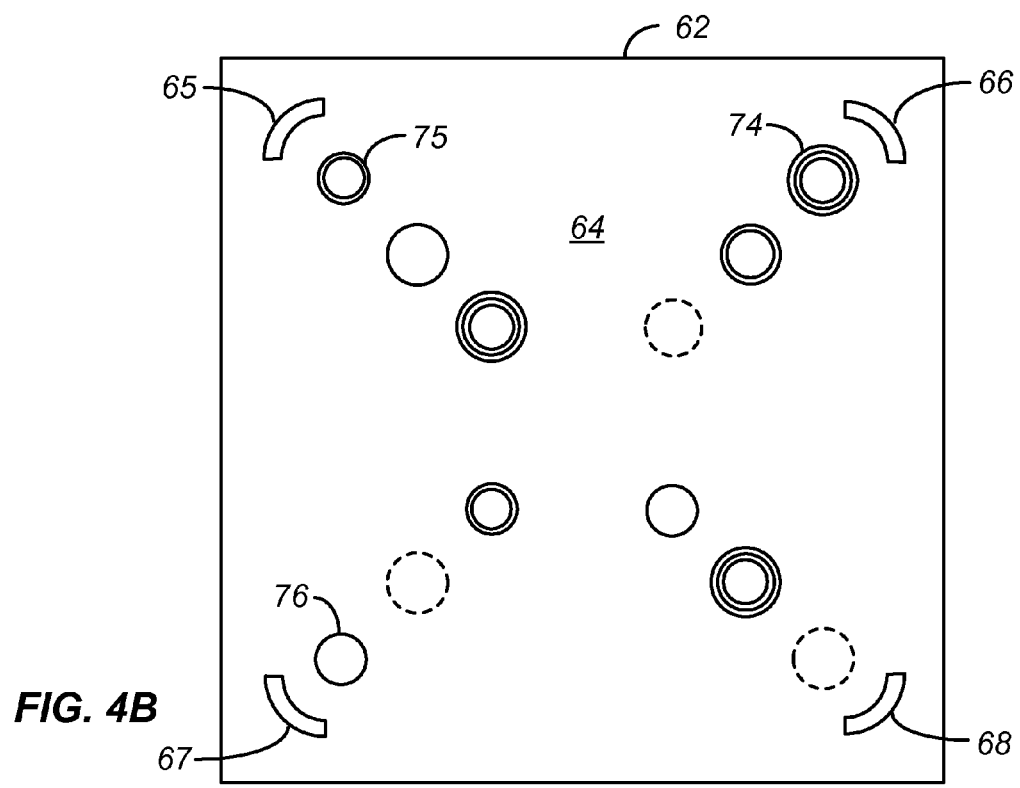

FIGS. 4A and 4B are depict an alternative configuration of a lower electrode plate 61 and base 62, respectively, showing the underside 63 of the lower electrode plate and the floor 64 of the base. This configuration offers four heights of the lower electrode plate over the base rather than two as in the configuration of FIGS. 2 and 3. The plate 61 and base 62 are both square rather than oblong rectangles, and the plate 61 can thus be placed in any one of four rotational orientations within the guides 65, 66, 67, 68 on the base floor. The plate 61 has three inverse lands 71, 72, 73. These inverse lands are arranged such that in one orientation they abut one set of lands 74 on the base (indicated by circles drawn with triple lines); in a second orientation with the plate 61 rotated 90 degrees from the first orientation, they abut a second set of lands 75 on the base (indicated by circles drawn with double lines); in a third orientation with the plate 61 rotated 90 degrees from the second, they abut a third set of lands 76 on the base (indicated by circles drawn with single lines); and in a fourth orientation with the plate 61 rotated 90 degrees from the third, they abut none of the lands on the base and instead fall in areas between the lands (indicated by circles with dashed lines). The lands in each set, both on the undersurface of the plate and on the floor of the base, are asymmetrically arranged around the axis of rotation 77 of the plate. When the lands on the base are of different heights, the four orientations will place the plate 61 at different heights above the base 62.

Figure 5A:
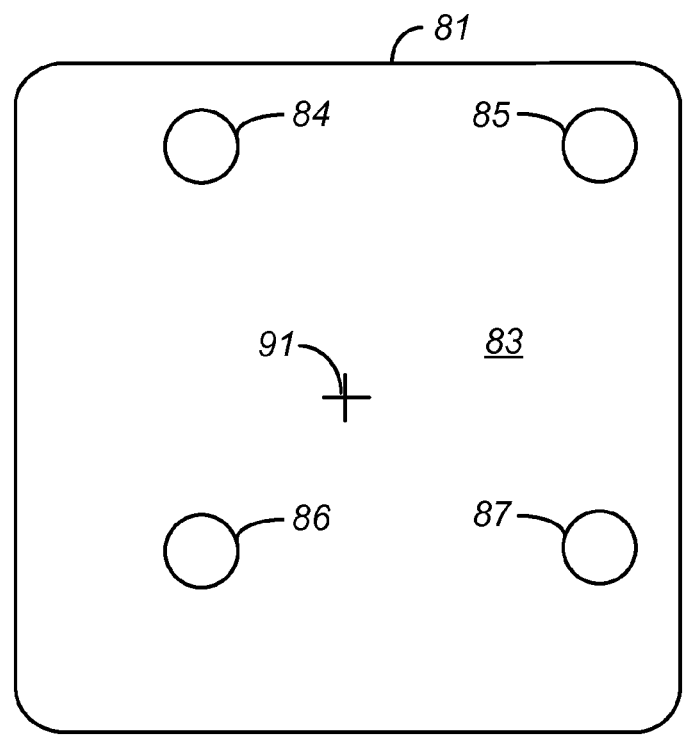
FIGS. 5A and 5B are plan views of the underside of the lower electrode plate and the floor of the base, respectively, as further alternatives to those of the preceding Figures.
Figure 5B:
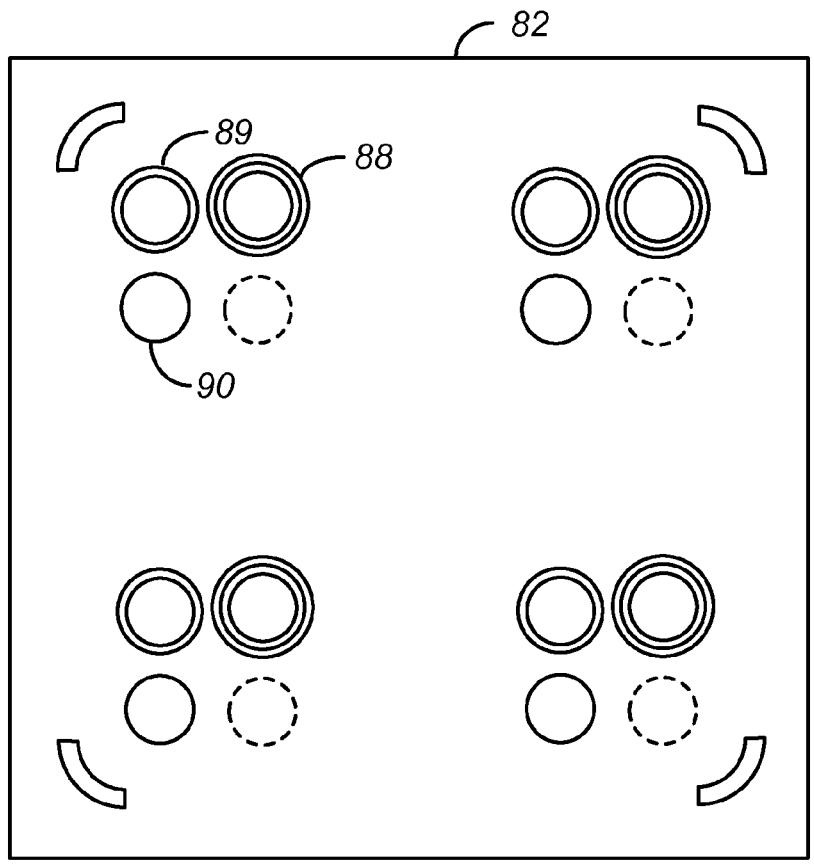

A still further configuration of lands is shown in FIGS. 5A and 5B. Here, as in FIGS. 4A and 4B, the lower electrode plate 81 and the base 82 are both square, allowing for four rotational orientations ninety degrees apart. The undersurface 83 of the plate contains four lands 84, 85, 86, 87 instead of three, and the base contains three corresponding sets of lands 88, 89, 90, the lands on the plate and each set of lands on the floor being asymmetrically arranged around the axis of rotation 91. The three sets of lands on the floor are at different heights, and rotation of the plate in increments of 90 degrees as in FIGS. 4A and 4B places the plate 81 at different heights above the base 82. In both the configuration of FIGS. 4A and 4B and that of FIGS. 5A and 5B, one or more sets of lands on the base floor can be replaced by indentations, with a similar effect.

Figure 6:
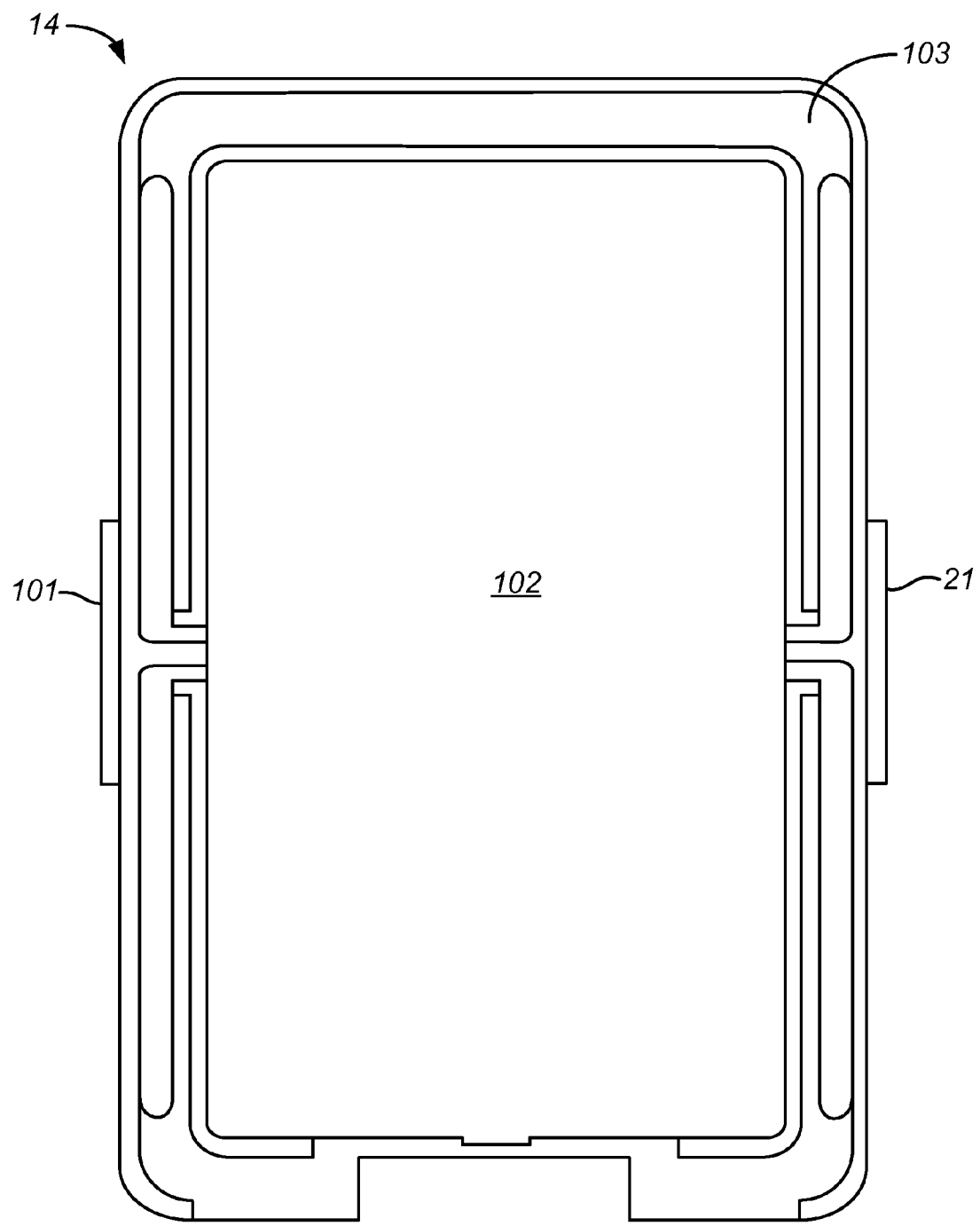
FIG. 6 is a plan view of the underside of the upper electrode plate of the cassette of FIG. 1.
Figure 7:
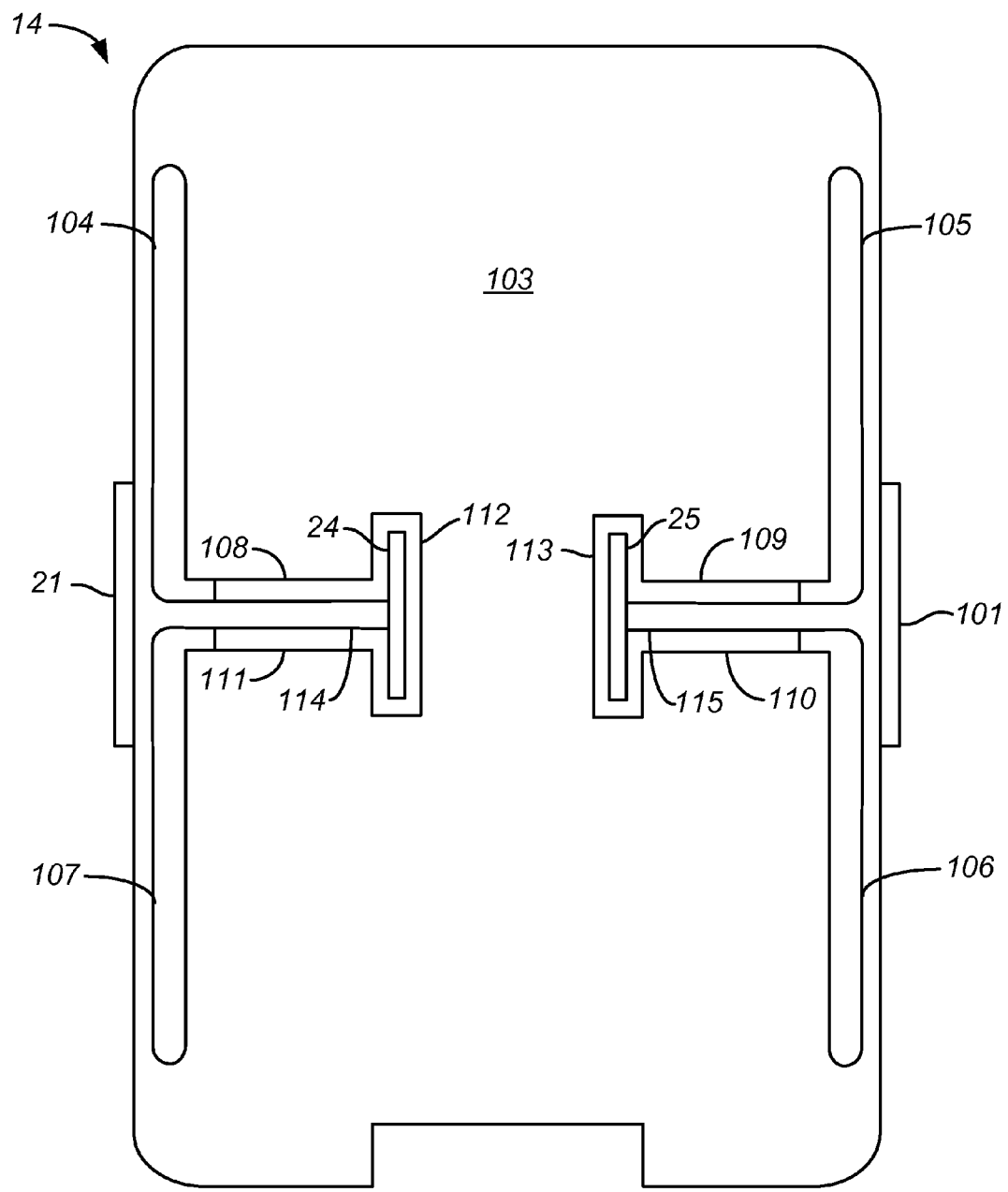
FIG. 7 is a plan view of the top of the upper electrode plate of FIG. 6.

Returning to the cassette with the oblong rectangular configuration of FIG. 1, plan views of the bottom and top of the upper electrode plate 14 are shown in FIGS. 6 and 7, respectively. The latch tab 21 shown in FIG. 1 is likewise shown in FIGS. 6 and 7, together with a second latch tab 101 protruding from the opposite edge of the plate such that the two latch tabs are symmetrically arranged on the plate. In the bottom view of FIG. 6, the upper electrode itself 102 is seen and is exposed downward. The electrode is mounted beneath a rigid flat sheet 103, best seen in FIG. 7. The sheet 103 is continuous except for elongated slots 104, 105, 106, 107 along the two longitudinal side edges of the plate, transverse slots 108, 109, 110, 111 that extend from the longitudinal slots part of the distance toward the center of the plate, and relatively short longitudinal slots 112, 113 at the inner termini of the transverse slots. Protruding inward from the two longitudinal edges of the plate and through the transverse slots 112, 113 are transverse bars 114, 115 that terminate in the finger tabs 24, 25 that are also visible in FIG. 1. The user can squeeze the finger lugs 24, 25 together between the user's thumb and forefinger, and by so doing will draw the latch tabs 21, 101 inward to retract them from the slots 22, 23 in the peripheral walls of the base. By squeezing the finger lugs 24, 25 in this manner, the user can remove the upper electrode plate 14 from the base. Conversely, the plate can be placed inside the base by first squeezing the tabs together and then releasing them once they are aligned with the slots. To allow movement of the finger lugs, the lugs and the transverse bars 114, 115 are not bonded to the underlying electrode plate 102 and are thereby free to be moved.

Electrical access to the two electrodes is achieved by exposed areas of the two electrodes at one end of each of the two electrode plates. In FIG. 1, the exposed area in the upper electrode is a short segment 121 bent at a right angle to the remainder of the electrode, the short segment facing an opening in the plate 14. The exposed area in the lower electrode is likewise a short segment that is bent at a right angle and exposed through an opening 122 in the periphery of the plate 13. Corresponding contacts in the instrument in which the cassette is inserted are arranged to provide electrical connections to these exposed areas.

Alternatives to the structures, shapes, and arrangements shown in the figures that are still within the concept of the present invention include the use of latches of configurations other than tabs and slots, the inclusion of fewer than two such latches or more than two, the use of lands of different shapes, indentations or apertures instead of lands, and the use of slits, shoulders, or the like instead of the elongated tabs that serve as guides for insertion of the cassette in the instrument. Still further variations will be readily apparent to those of skill in the art.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is not excluded from the scope of the claim. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An electroblotting cassette comprising a lower electrode plate, an upper electrode plate, a base to support said lower and upper electrode plates, manually releasable securing means for securing said upper electrode plate to said base over said lower electrode plate, and spacing means for allowing a user to select among a plurality of heights of said lower electrode plate within said base by placing said lower electrode plate in different rotational orientations relative to said base.

2. The electroblotting cassette of claim 1 wherein said upper electrode plate is comprised of a plate electrode mounted to an electrically non-conducting support plate, and said manually releasable securing means comprise a pair of finger lugs on said support plate positioned such that said finger lugs are capable of being grasped by a thumb and forefinger, respectively, of a single hand of a user.

3. The electroblotting cassette of claim 1 wherein said upper electrode plate is comprised of a plate electrode mounted to an electrically non-conducting support plate, said base has a raised peripheral wall, and said manually releasable securing means comprise (i) a pair of tabs resiliently mounted to said non-conducting support plate and extending from said support plate in opposite directions, and (ii) a pair of slots in said peripheral wall of said base aligned with said tabs when said upper electrode plate is placed within said peripheral wall.

4. The electroblotting cassette of claim 1 wherein:
(a) said upper electrode plate is comprised of a plate electrode mounted to an electrically non-conducting support plate, and said manually releasable securing means comprise a pair of resilient strips joined to said support plate at opposing parallel sides of said support plate, each strip having a tab extending outward from said support plate and a finger lug for bending said strip and thereby displacing said tab, and
(b) said base has a raised peripheral wall and slots in said peripheral wall aligned with said tabs when said upper electrode plate is placed within said peripheral wall.

5. The electroblotting cassette of claim 1 wherein:
(a) said base has a floor and said lower electrode plate has an undersurface, and
(b) said spacing means comprise an array of flat-surfaced base-mounted projections extending upward from said floor of said base and a corresponding array of flat-surfaced plate-mounted projections extending downward from said undersurface of said lower electrode plate, said base-mounted projections and said plate-mounted projections arranged such that said base-mounted projections abut said plate-mounted projections when said lower electrode plate is positioned over said base in a first rotational orientation relative to said base and said base-mounted projections are offset from said plate-mounted projections when said lower electrode plate is positioned over said base in a second rotational orientation relative to said base.

6. The electroblotting cassette of claim 5 wherein said base and said lower electrode plate are rectangular, said spacing means comprise four said base-mounted projections and four said plate-mounted projections, and said first rotational orientation and said second rotation orientation being 180 degrees apart.

7. The electroblotting cassette of claim 5 wherein said base and said lower electrode plate are rectangular, and said base further comprises guides projecting from said floor to center said lower electrode plate over said base and to restrict said lower electrode plate to either two or four rotational orientations relative to said base.

8. The electroblotting cassette of claim 7 wherein said guides restrict said lower electrode plate to two rotational orientations 180 degrees apart.

9. A method for transferring electrophoretically separated species from a gel to a membrane, said method comprising:
(a) placing a lower electrode plate at a selected height above a base by selecting a rotational orientation of said lower electrode plate relative to said base that corresponds to said selected height, said lower electrode plate and said base together having spacing means that vary said height according to said rotational orientation,
(b) placing said gel and said membrane over said lower electrode plate,
(c) placing an upper electrode plate over said gel and said membrane while securing said upper electrode plate at a fixed height above said base by manually releasable securing means securing said upper electrode plate to said base, and
(d) imposing a voltage between said lower electrode plate and said upper electrode plate to cause electroblotting of said species from said gel to said membrane.

10. The method of claim 9 wherein said upper electrode plate is comprised of a plate electrode mounted to an electrically non-conducting support plate, and said manually releasable securing means comprise a pair of finger lugs on said support plate, and step (c) comprises grasping said finger lugs by a thumb and forefinger, respectively, of a single hand of a user, and releasing said finger lugs once said upper electrode plate is in position.

11. The method of claim 9 wherein said upper electrode plate is comprised of a plate electrode mounted to an electrically non-conducting support plate, said base has a raised peripheral wall with slots therein on opposing sides of said base, and said manually releasable securing means comprise a pair of tabs resiliently mounted to said non-conducting support plate and extending from said support plate in opposite directions to engage said slots, and step (c) comprises retracting said tabs to insert said upper electrode plate within said peripheral wall, and releasing said tabs to cause said tabs to engage said slots once said upper electrode plate is so inserted.

12. The method of claim 9 wherein said upper electrode plate is comprised of a plate electrode mounted to an electrically non-conducting support plate, said base has a raised peripheral wall with slots therein, and said manually releasable securing means comprise a pair of finger lugs on said support plate and a pair of tabs resiliently mounted to said support plate and extending from said support plate to engage said slots, and step (c) comprises retracting said tabs by compressing said finger lugs to insert said upper electrode plate within said peripheral wall, and releasing said finger lugs to cause said tabs to engage said slots once said upper electrode plate is so inserted.

* * * * *